United States Patent [19]
Goodenough et al.

[11] Patent Number: 5,164,978
[45] Date of Patent: Nov. 17, 1992

[54] TEST BODY AND ELEMENT FOR A SCANNING IMAGE RECONSTRUCTING APPARATUS

[75] Inventors: David J. Goodenough, Myersville, Md.; Joshua R. Levy, Salem, N.Y.

[73] Assignee: The Phantom Laboratory, Incorporated, Salem, N.Y.

[21] Appl. No.: 616,344

[22] Filed: Nov. 21, 1990

[51] Int. Cl.⁵ .................................. G01D 18/00
[52] U.S. Cl. ........................ 378/207; 378/204; 250/252.1
[58] Field of Search ............ 378/18, 207, 204; 73/1 DV; 250/252.1 R

[56] References Cited

U.S. PATENT DOCUMENTS

| | | | |
|---|---|---|---|
| 3,310,885 | 3/1967 | Alderson | 35/17 |
| 4,028,545 | 6/1977 | Foster | 378/207 |
| 4,055,771 | 10/1977 | Goodenough et al. | 378/145 |
| 4,126,789 | 11/1978 | Vogl et al. | 250/505 |
| 4,296,329 | 10/1981 | Mirabella | 250/491 |
| 4,344,183 | 8/1982 | Jacobson | 378/207 |
| 4,551,678 | 11/1985 | Morgan et al. | 324/300 |
| 4,613,754 | 9/1986 | Vinegar et al. | 250/252.1 |
| 4,618,826 | 10/1986 | Smith et al. | 324/308 |
| 4,625,168 | 11/1986 | Meyer et al. | 324/300 |
| 4,644,276 | 2/1987 | Sierocuk et al. | 324/307 |
| 4,692,704 | 9/1987 | Gray | 324/318 |
| 4,698,836 | 10/1987 | Minasian | 378/162 |
| 4,782,502 | 11/1988 | Schulz | 378/18 |
| 4,818,943 | 4/1989 | Chandra | 324/318 |
| 4,870,666 | 9/1989 | Lonn et al. | 378/18 |
| 4,873,707 | 10/1989 | Robertson | 378/18 |
| 4,972,451 | 11/1990 | Brok et al. | 378/207 |

Primary Examiner—Janice A. Howell
Assistant Examiner—Don Wong
Attorney, Agent, or Firm—Heslin & Rothenberg

[57] ABSTRACT

The subject invention provides a means for testing the operating characteristics of an image reconstructing apparatus, the means including a high resolution gauge for determining the resolution of the apparatus and including a bead which is adapted for testing the modulation transfer function of the apparatus. A method of producing the high resolution gauge is also provided.

18 Claims, 3 Drawing Sheets

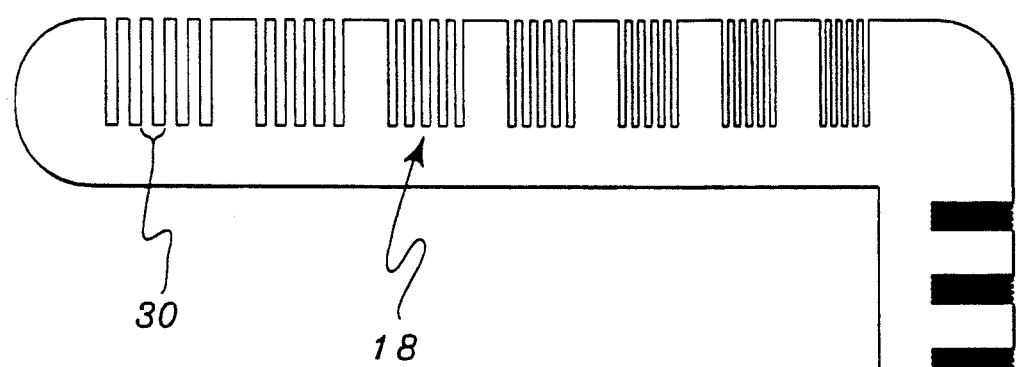
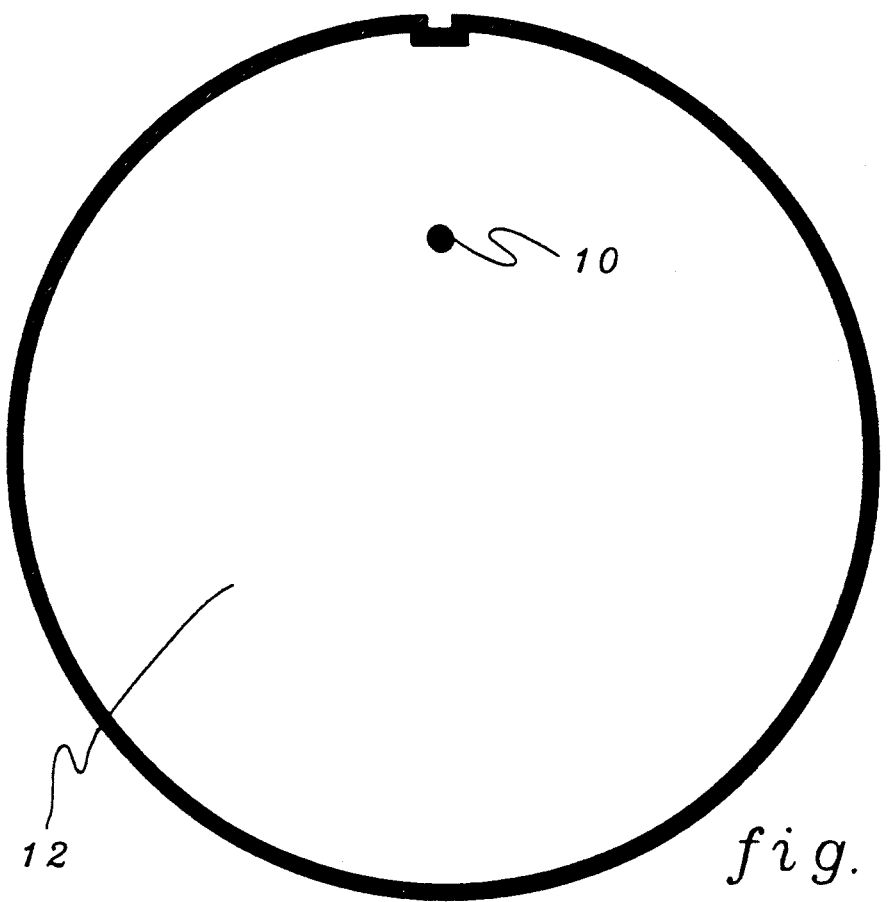
fig. 3
fig. 1

TEST BODY AND ELEMENT FOR A SCANNING IMAGE RECONSTRUCTING APPARATUS

FIELD OF THE INVENTION

This invention relates to equipment used to reconstruct an image of the interior of a subject across a plane. The invention relates more particularly to a test body and element for testing the operating characteristics of such equipment and a method for producing such test elements.

BACKGROUND OF THE INVENTION

Numerous types of medical equipment, as is well known, are used to reconstruct an image of the interior of a subject across a plane. Examples of such medical equipment include x-ray tomographic scanners, magnetic resonance imaging scanners, and nuclear medicine emission computed tomography (ECT) scanners. Each of these scanners are used to reconstruct an image of a cross section, or slice, through a patient's body. Consecutive cross sectional images are then combined to create an image of the interior of a subject.

Tomography is a medical technique of radiographic analysis which provides an image of a particular plane of a body under examination. In one form of tomographic instrument known as a CAT scanner (computed axial tomography), an x-ray source and x-ray detectors are positioned in alignment on opposite sides of a subject under examination and simultaneously scan an edge of a cross sectional plane or slice of finite thickness extending through the subject.

Intensity of x-ray transmission through the subject is determined by sampling an electrical output of the detectors. Sampling occurs in numerous locations in the direction of a single scan. The x-ray source is then rotated a predetermined angular distance about an axis normal to the plane or slice through the subject and another scanning of the edge in a different direction is obtained. Resultant data is processed by a computer to reconstruct an image of the planer cross-section or slice through the patient's body.

In another form of image reconstruction known as magnetic resonance imaging (MRI), the body of a subject is placed within a magnetic field. When a radio-frequency at the resonance (Larmor) frequency is applied to the subject within the magnetic field, the magnetic moment of the subject's atoms which are normally in random alignment align in a north and south direction relative to the magnetic field. When the radiofrequency is terminated, the atoms return to their random alignment and in so returning will emit energy via a radiofrequency at the same resonance frequency. This radiofrequency is detected via an antenna and the resultant data generated by the detection can be analyzed into contributing frequencies and processed by a computer to reconstruct an image in cross section of the patient's body. This form of image reconstruction is also known as nuclear magnetic resonance (NMR) imaging.

Image reconstructing apparatuses include such CAT scanners, MRI or NMR scanners, ECT scanners, and any apparatus that receives data and processes it to create an image in cross section of the patient's body.

It is desirable at times to verify that the operation of an instrument for reconstructing an image of the interior of a subject conforms with its known capabilities. In addition, it is desirable to predetermine the capabilities of the instrument for the performance of specific examinations.

A test body (phantom) for determining the operating characteristics of a scanning tomographic analytical apparatus of the type known as a CAT scanner is disclosed in co-assigned U.S. Pat. No. 4,055,771, issued Oct. 25, 1977 to Goodenough et al. The contents of this U.S. Patent in its entirety are hereby incorporated into this application in order to more fully define the state of the art to which the subject invention pertains. The test body comprises energy absorption means arranged in layered arrays extending generally parallel to a direction of projection of the x-ray beam, and means for positioning the energy absorbing means between a scanning x-ray beam and a transmission intensity detector of the tomographic apparatus.

A phantom for determining the operating characteristics of a nuclear magnetic resonance scanner is disclosed in U.S. Pat. No. 4,644,276, issued Feb. 17, 1987 to Newman and Sierocuk. The phantom comprises at least two test plates which include means for testing parameters of the scanner and allows the scanner to be tested in the plane in which these test plates lie.

Another phantom for determining the operating characteristics of a magnetic resonance imaging scanner is disclosed in U.S. Pat. No. 4,692,704, issued Sep. 8, 1987 to Gray. The phantom includes a generally tubular body containing a cylindrical stack of a plurality of leaves. Each leaf has one or more wedge shaped slices or sectors cut out for identification and reference purposes.

These test bodies, or phantoms, used for determining the operating characteristics of an image reconstructing apparatus often include at least one test element adapted for testing the resolution of the apparatus. One such test element comprises a resolution gauge having line pairs of predetermined width. These resolution gauges have been cut from plastic of varying densities and some metals. The technologies used to cut plastic resolution gauges were pushed to the limit of standard machining tolerances to produce accurate resolution of eleven line pair per centimeter (line pair). As the technology of image reconstructing apparatuses has improved and progressed, the high resolution of such apparatuses has increased to greater levels. The new image reconstructing apparatuses require high resolution running up to twenty line pair per centimeter. To achieve the tolerances necessary to create accurate tests for resolution above eleven line pair, different technologies of cutting materials were required.

The subject invention has solved this problem by providing a test element adapted for testing the resolution of the apparatus produced by using a wire electrical discharge machine in order to cut line pairs of predetermined width into metal. Using this technology, line pairs up to twenty line pairs per centimeter are achieved. Additionally, plastic resolution gauges have been obtained by using laser technology to cut line pairs in plastic. These plastic resolution gauges are able to be cut up to eleven to thirteen line pairs per centimeter. Use of the wire electrical discharge machine and the laser technology have provided resolution gauges which solve the problems required by the high resolution obtainable with image reconstruction apparatuses.

Test bodies for determining the operating characteristics of image reconstruction apparatuses also often include at least one test element adapted for testing the modulation transfer function of the apparatus. The test element, as disclosed in co-assigned U.S. Pat. No. 4,055,771, previously comprised a cylindrical wire which is used to create a small point in a scanned image which will generate the information required to calculate the modulation transfer functions. As the resolution of image reconstructing apparatuses increased dramatically, dimensionally smaller and more symmetrical point sources were required. The wire type point source is positioned perpendicular to the scan plane, creating a small cross sectional footprint of the scan image. However, if the wire is not maintained in a perpendicular position to the z axis, the image created when the wire is scanned through the xy plane will be oval instead of circular, and often leads to streak artifacts. This elongation will reduce the accuracy of the MTF calculation.

The subject invention provides a bead which is used as the impulse point source for modulation transfer function. The bead is three dimensionally symmetrical which eliminates the z axis alignment positioning dependency which is required with the cylindrical wire. The bead size and shape eliminate the requirements for exact perpendicular alignment to the z axis, reducing the requirement for accurate alignment. This is especially helpful in daily quality assurance checks when the technician is rushed and unable to take the time for careful alignment, and when the image evaluation is being performed by a computer and the technician may not be aware of the critical nature of proper positioning. The subject invention thus solves the problems associated with previous cylindrical wires used as point sources for modulation transfer function.

SUMMARY OF THE INVENTION

Accordingly, it is an object of the subject invention to provide an improved means for testing the operation of an image reconstructing instrument. Another object of the invention is to provide an improved phantom (test body) for verifying operating characteristics of an image reconstructing instrument.

More specifically, it is an object of the subject invention to provide a test body for determining an operating characteristic of an image reconstructing apparatus wherein the test body includes at least one test element adapted for testing the resolution of the apparatus, the test element comprising line pairs of predetermined width, wherein the number of line pairs per unit length varies in the direction of scoring and the number is up to about twenty line pairs per centimeter.

It is an object of the subject invention to provide such a high resolution gauge made of metal which is cut with wire electrical discharge machines or which is plastic and is cut with laser technology.

It is an object of the subject invention to provide such high resolution gauges in order to provide for finer resolution at higher accuracy than other gauges. It is an object of the subject invention to provide such high resolution gauges which are protected from damage, eliminate water variables, and eliminate water bubble collection between line pairs by casting such gauges in epoxy.

It is a further object of the subject invention to provide high resolution gauges which are arranged in an L pattern to prevent the streaking artifacts of one test from distorting the information from the next. It is an object of the subject invention to provide a high resolution gauge having corners which are rounded in order to reduce edge artifacts.

A further object of the subject invention is to provide a test body for determining an operating characteristic of an image reconstructing apparatus wherein the test body includes at least one test element adapted for testing the modulation transfer function of the apparatus, the test element comprising a bead.

It is a further object of the subject invention to provide an impulse point source for modulation transfer function which does not depend upon the z axis alignment for proper positioning. It is a further object of the subject invention to provide such an impulse point source which does not lead to streak artifacts. It is an object of the subject invention to provide an impulse point source which reduces the requirement for accurate alignment in daily quality assurance checks and when rapid testing of the equipment is required.

In accordance with the features of this invention, a test body is provided for determining an operating characteristic of an image reconstructing apparatus wherein the test body includes at least one test element adapted for testing the resolution of the apparatus, the test element comprising line pairs, the line pairs being of predetermined width, wherein the number of line pairs per unit length varies in the direction of scoring.

A test body is also provided for determining an operating characteristic of an image reconstructing apparatus wherein the test body includes at least one test element adapted for testing the modulation transfer function of the apparatus, the test element comprising a bead.

Also provided is a method of producing a plastic test element adapted for testing the resolution of an image reconstructing apparatus, the method comprising the steps of using a laser to cut line pairs of predetermined width into a plastic material and varying the number of line pairs per unit length in the direction of scoring, so as to produce a plastic test element.

Further provided is a method of producing a metal test element adapted for testing the resolution of an image reconstructing apparatus, the method comprising the steps of using a wire electrical discharge machine to cut line pairs of predetermined width into metal and varying the number of line pairs per unit length in the direction of scoring, so as to produce a metal test element.

Scanning of the test body and test elements of the subject invention with the image reconstructing apparatus provides images, which when compared to predetermined images enable determination of particular characteristics of the apparatus. Such characteristics include resolution of the apparatus at various contrast levels and the generation of the data for the determination of the modulation transfer function from a point spread function of the apparatus.

BRIEF DESCRIPTION OF THE FIGURES

These and other objects, features, and advantages of the subject invention will be evident from the following detailed description when read in conjunction with the accompanying drawings in which:

FIG. 1 is a top view of a tungsten carbide bead cast in an epoxy plate which is one embodiment of the test element of the subject invention adapted for testing the modulation transfer function of an apparatus.

FIG. 3 is a top view of the high resolution gauge shown in FIG. 2.

DETAILED DESCRIPTION OF THE INVENTION

Figure 2:
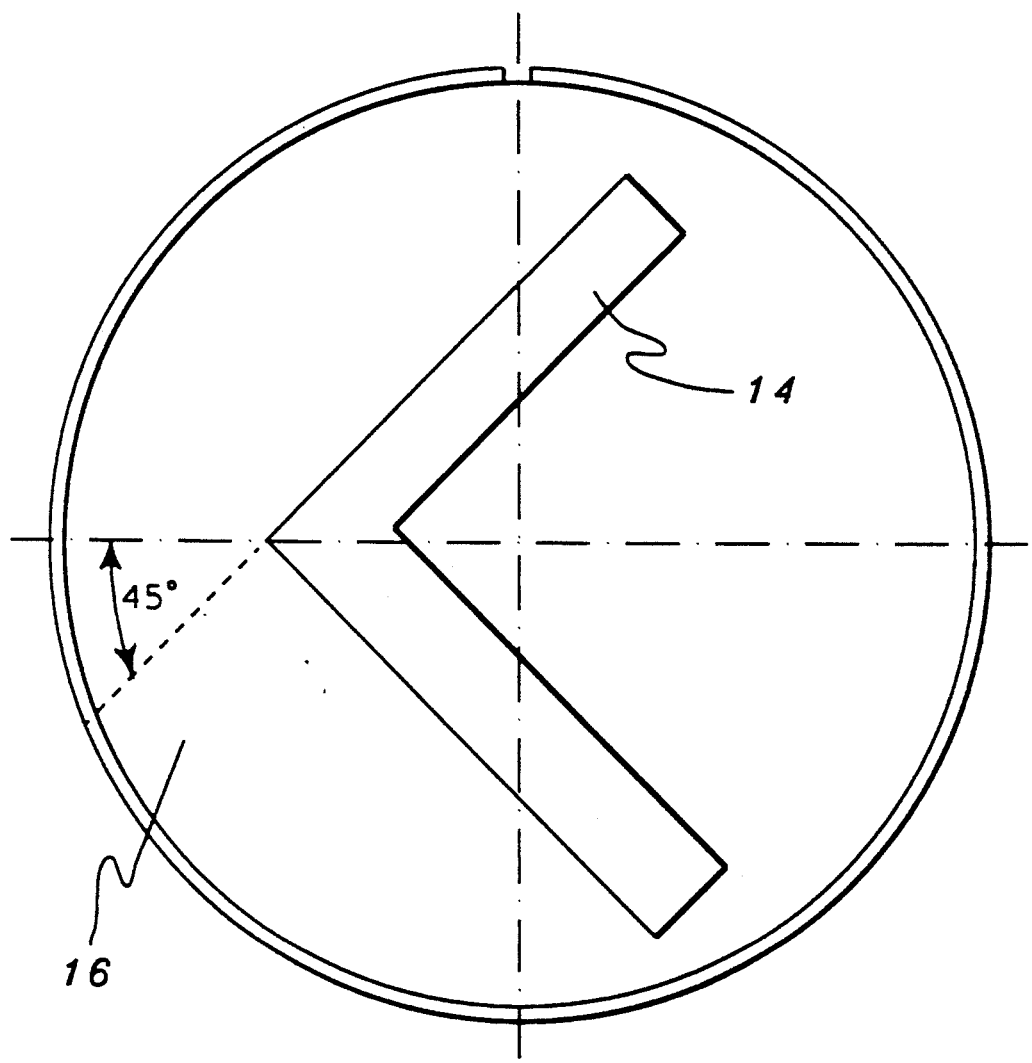
FIG. 2 is a top view of a high resolution gauge cast in epoxy which is one embodiment of the test element of the subject invention adapted for testing the resolution of an apparatus.
Figure 4:
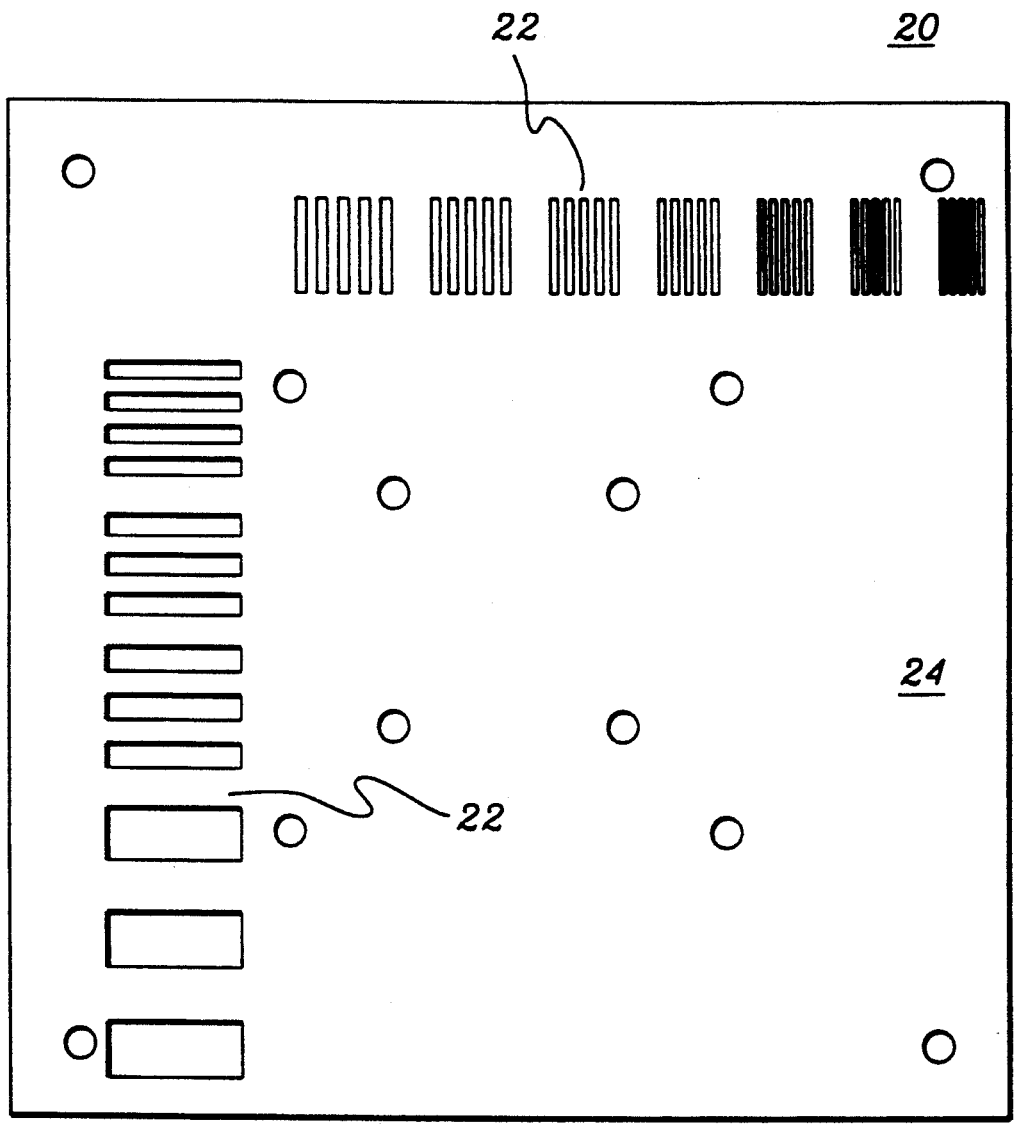
FIG. 4 is a top view of a high resolution gauge which is another embodiment of the test element of the subject invention adapted for testing the resolution of the apparatus.

As indicated hereinbefore, it is desirable at times to determine and verify the operating characteristics of an image reconstructing apparatus. These characteristics include the resolution of the apparatus and the generation of the data for the determination of the modulation transfer function from the point spread function of the apparatus.

Accordingly, the subject invention provides high resolution gauges and a method of manufacturing them. The high resolution gauges are produced by cutting material with laser cutters or wire electrical discharge machines (EDM). Wire EDM and laser cutting equipment are used to cut precision slots in metal and plastics for use in measuring the resolution of image reconstructing apparatuses, such as CAT scanners and MRI systems.

The subject invention provides a high resolution gauge (14, 20) produced by cutting plastic material (20) with laser cutters or metal (14) with wire electrical discharge machines.

The high resolution gauge (14) has up to twenty line pair (18) per centimeter. Line paris (18), referring to FIG. 3, are defined based on the width of a space and a "tooth" on the resolution gauge. One line pair (30) comprises the space and the tooth. Twenty line Pairs per centimeter indicates that twenty of these line pairs (30) can be cut in a one centimeter distance. Slot width on the resolution gauge indicates the width of a slot, i.e. the width of a space between teeth. Each tooth is generally the same width as its adjacent slot width.

The direction of scoring of the resolution gauge, referring again to FIG. 3, means that the line pair per unit length varies as you move along the gauge. For example, the direction of scoring proceeds from slot widths 0.0394 to 0.0328 to 0.0281, etc. On the perpendicular side of the resolution gauge, the direction of scoring proceeds, for example, from slot widths 0.0164 to 0.0151 to 0.0141, etc. These varying slot widths produce line pairs of varying sizes, for example a slot width of 0.0098 is equivalent to twenty line pairs per centimeter.

The high resolution gauge is cut from aluminum. The density of the aluminum is much greater than soft tissue, therefore the size of the aluminum is thinner than the scan thickness of the apparatus. The density of the aluminum is averaged with the surrounding epoxy material (16) in which the aluminum gauge is cast to eliminate a problem of extreme density overloading. The contrast of the epoxy (16) and the aluminum (14) creates the resolution pattern. The aluminum gauge could also be used in a water bath phantom, wherein the contrast between water and aluminum would create the resolution pattern.

Plastic resolution gauges (20) are also provided which are cut with lasers. Up to eleven to thirteen line pairs (22) per centimeter can be obtained using laser cutters. The plastic high resolution gauge (20) can also be cast in epoxy (24).

The subject invention further provides an impulse point source bead (10) for determining modulation transfer function. The bead (10) consists of a small 0.011 inch tungsten carbide bead. Any equivalent small, high density bead could also be used in the subject invention. The bead is constructed out of any high density material and is sized so that it will not, under normal use, cover more than one pixel point. The bead is suspended in the scan field and surrounded by a homogeneous material, such as cast in a cylindrical disc with the bead imbedded into epoxy material (12). The bead is used to create a small point in a scan image which will generate the information required to calculate the modulation transfer functions.

By its symmetrical form the bead prevents ovalling and streaking which would elongate the MTF curve, thus distorting the values.

Another advantage of the bead is in ease of manufacturing. To suspend a wire which is perfectly perpendicular to the phantom axis requires expensive machining and fixtures which will hold the wire at either end within a couple thousandths of an inch. By using the spherical bead, there is no critical orientation so the casting and fixturing becomes very simple.

Although preferred embodiments have been depicted and described in detail herein, it will be apparent to those skilled in the relevant art that various modifications, additions, substitutions and the like can be made without departing from the spirit of the invention, and these are therefore considered to be within the scope of the invention as defined by the following claims.

What is claimed is:

1. A test body for determining an operating characteristic of an image reconstructing apparatus, wherein said test body includes at least one test element for testing the resolution of the apparatus, the test element comprising direction of scoring line pairs, said lien paris being of predetermined width, wherein the number of liens pairs per unit length varies in the direction of scoring from about twelve line pairs per centimeter to about twenty line pairs per centimeter.

2. The test body of claim 1, wherein said test element is casting epoxy.

3. The test body of claim 1, wherein said rest element is cut from metal.

4. The test body of claim 3, wherein said metal comprises aluminum.

5. A test body for determining an operating characteristic of an image reconstructing apparatus, wherein said rest body includes at least one test element for testing the resolution of an apparatus, the test element being cut from plastic and comprising direction of scoring and line pairs, said line pairs being of predetermined width, wherein the number of line pairs per unit length is up to about thirteen line pairs per centimeter and varies in the direction of scoring.

6. A system for determining an operating characteristic of an image reconstructing apparatus, said system comprisign a test body positioned within an image reconstructing apparatus, wherein said test body includes at least one test element for testing the modulation transfer function of the apparatus, the test element comprising a bead which is positioned within the test body in a fixed position relative to said test body.

7. The test body of claim 6, wherein the bead comprises a tungsten carbide bead.

8. A test element for testing the resolution of an image reconstructing apparatus, said test element comprising direction of scoring and line pairs, said lien pairs being of predetermined width, wherein the number of liens pairs per unit length varies in the direction of scoring from about twelve line pairs per centimeter to about twenty line pairs per centimeter.

9. The test element of claim 8, wherein said first element is cast in epoxy.

10. The test element of claim 8, wherein said test element is cut from metal.

11. The test element of claim 10, wherein said metal comprises aluminum.

12. A test element for testing the resolution of an image reconstructing apparatus, said rest element being cut from plastic and comprising direction of scoring and line pairs, said line pairs being of predetermined width, wherein the number of line pairs per unit length is up to about thirteen line pairs per centimeter and varies in the direction of scoring.

13. A method of producing a plastic test element for testing the resolution of an image reconstructing apparatus, wherein said rest element comprising direction of scoring, said method comprisign the steps of using a laser to cut line pairs of a predetermined width into a plastic material, and varying the number of line pairs per unit length in the direction of scoring, said number of line pairs per unit length being up to about thirteen line pairs per centimeter, so as to produce a plastic test element.

14. The method of claim 13, further comprising casting said plastic test element in epoxy.

15. A method of producing a test element for testing the resolution of an image reconstructing apparatus, wherein said test element comprising direction of scoring, said method comprising the steps of using a wire electrical discharge machine to cut line pairs of predetermined width into metal, and varying the number of line pairs per unit length in the direction of scoring, said number of lien pairs per unit length being up to about twenty line pairs per centimeter, so as to produce a metal test element.

16. The method of claim 15, further comprising casting said metal test element in epoxy.

17. The method of claim 16, wherein said metal comprises aluminum.

18. A method of determining the modulation transfer function of an image reconstructing apparatus, said method using a test body which includes at least one test element for testing the modulation transfer function of the apparatus, the test element comprising a bead, said method comprisign the steps of:

positioning said test body within said apparatus, thereby positioning said bead test element within said apparatus;

operating said apparatus so as to generated 5a for calculating the modulation transfer function of the apparatus, said data being generated by scanning said bead test element; and calculating said modulating transfer function of said apparatus from said generated data.

* * * * *

UNITED STATES PATENT AND TRADEMARK OFFICE
CERTIFICATE OF CORRECTION

PATENT NO. : 5,164,978                  Page 1 of 2

DATED : November 17, 1992

INVENTOR(S) : David J. Goodenough et al

It is certified that error appears in the above-indentified patent and that said Letters Patent is hereby corrected as shown below:

Column 6

```
In claim 1, line 5, after "of scoring" add --and--;
            line 5, change "lien paris" to --line pairs--; and
            line 7, change "liens" to --lines--.
In claim 2, line 2, change "casting" to --cast in--.
In claim 3, line 1, change "rest" to --test--.
In claim 5, line 3, change "rest" to --test--; and
            line 4, change "an apparatus" to --the apparatus--.
In claim 6, line 3, change "comprisign" to --comprising--.
```

Column 7

```
In claim 8,  line 3, change "lien" to --line--; and
             line 4, change "liens" to --line--.
In claim 9,  line 1, change "first" to --test--.
In claim 12, line 2, change "rest" to --test--.
In claim 13, line 3, change "rest" to --test--; and
             line 4, change "comprisign" to --comprising--.
```

UNITED STATES PATENT AND TRADEMARK OFFICE
CERTIFICATE OF CORRECTION

PATENT NO. : 5,164,978
DATED : November 17, 1992
INVENTOR(S) : David J. Goodenough et al It is certified that error appears in the above-indentified patent and that said Letters Patent is hereby corrected as shown below:

Column 8

In claim 15, line 8, change "lien" to --line--.
In claim 18, line 6, change "comprisign" to --comprising--;
line 10, change "generated 5a" to --generate data--; and
line 14, change "modulating" to --modulation--.

Signed and Sealed this

Twelfth Day of October, 1993

Attest:

BRUCE LEHMAN

*Attesting Officer*    *Commissioner of Patents and Trademarks*